United States Patent
Juloski et al.

(10) Patent No.: US 9,283,044 B2
(45) Date of Patent: Mar. 15, 2016

(54) SOLENOID SYSTEM FOR MAGNETICALLY GUIDED CAPSULE ENDOSCOPY

(75) Inventors: Aleksandar Juloski, Nürnberg (DE); Johannes Reinschke, Nürnberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 559 days.

(21) Appl. No.: 13/393,417

(22) PCT Filed: Aug. 25, 2010

(86) PCT No.: PCT/EP2010/062365
§ 371 (c)(1),
(2), (4) Date: May 21, 2012

(87) PCT Pub. No.: WO2011/023710
PCT Pub. Date: Mar. 3, 2011

(65) Prior Publication Data
US 2012/0232337 A1   Sep. 13, 2012

(30) Foreign Application Priority Data
Aug. 31, 2009  (DE) .......................... 10 2009 039 484

(51) Int. Cl.
H01F 5/00 (2006.01)
A61B 19/00 (2006.01)

(52) U.S. Cl.
CPC ......... *A61B 19/22* (2013.01); *A61B 2019/2253* (2013.01); *A61B 2019/2265* (2013.01)

(58) Field of Classification Search
CPC .................................................. A61B 19/5244
USPC ........................................... 335/299; 600/424
See application file for complete search history.

(56) References Cited

U.S. PATENT DOCUMENTS

| | | | |
|---|---|---|---|
| 3,358,676 A | | 12/1967 | Frei et al. |
| 5,592,939 A | * | 1/1997 | Martinelli ...................... 600/424 |
| 6,493,573 B1 | * | 12/2002 | Martinelli et al. ............. 600/424 |
| 6,701,179 B1 | * | 3/2004 | Martinelli et al. ............. 600/424 |
| 8,235,888 B2 | * | 8/2012 | Kawano ......................... 600/118 |

(Continued)

FOREIGN PATENT DOCUMENTS

| | | |
|---|---|---|
| CN | 1929773 | 3/2007 |
| DE | 103 40 925 B3 | 6/2005 |

(Continued)

OTHER PUBLICATIONS

Chinese Office Action for related Chinese Patent Application No. 201080038717.5, issued Jan. 2, 2014, 4 pages.

(Continued)

*Primary Examiner* — Alexander Talpalatski
(74) *Attorney, Agent, or Firm* — Staas & Halsey LLP

(57) ABSTRACT

A solenoid system for magnetically guided capsule endoscopy, has the following components arranged under a patient table which defines a flat plane: a central coil with normal direction being perpendicular to the flat plane, and four coil pairs arranged in the form of a cross around the central coil with respect to the flat plane. Each pair includes two single coils, the normal directions of which are parallel to the flat plane and offset by 90 degrees in relation to each other.

20 Claims, 2 Drawing Sheets

(56) References Cited

U.S. PATENT DOCUMENTS

| | | |
|---|---|---|
| 2004/0244636 A1 | 12/2004 | Meadow, Jr. et al. |
| 2005/0216231 A1 | 9/2005 | Aoki et al. |
| 2007/0270628 A1 | 11/2007 | Kawano et al. |
| 2010/0010305 A1* | 1/2010 | Kawano .................. 600/118 |

FOREIGN PATENT DOCUMENTS

| | | |
|---|---|---|
| DE | 10 2007 007 801 A1 | 8/2008 |
| DE | 10 2008 004 871 A1 | 7/2009 |
| DE | 10 2009 039 484.2 | 8/2009 |
| JP | 2006-68501 | 3/2006 |
| WO | 02/49705 A1 | 6/2002 |
| WO | 2006/014011 A1 | 2/2006 |
| WO | 2007/077922 | 7/2007 |
| WO | 2009/089992 A1 | 7/2009 |
| WO | 2011/118253 | 9/2011 |

OTHER PUBLICATIONS

German Language Japanese Office Action for related Japanese Patent Application No. 2012-526043, issued Oct. 18, 2013, 6 pages.

English language International Search Report for PCT/EP2010/062365, mailed Jan. 20, 2011.

German Office Action for German Priority Patent Application No. 10 2009 039 484.2, issued on Jul. 8, 2010.

* cited by examiner

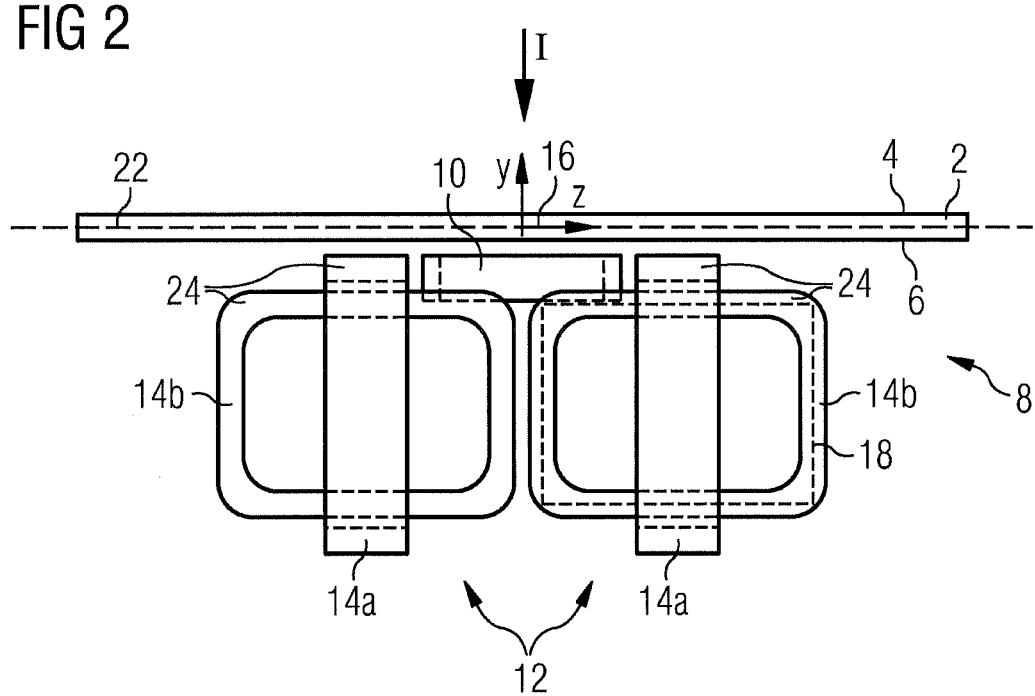

SOLENOID SYSTEM FOR MAGNETICALLY GUIDED CAPSULE ENDOSCOPY

CROSS REFERENCE TO RELATED APPLICATIONS

This application is based on and hereby claims priority to International Application No. PCT/EP2010/062365 filed on Aug. 25, 2010 and German Application No. 10 2009 039 484.2 filed on Aug. 31, 2009, the contents of which are hereby incorporated by reference.

BACKGROUND

An endoscopy capsule, which can fulfill various medical objectives, is introduced into a patient in magnetically guided capsule endoscopy (MGCE). The capsule contains a magnetic element, by which a force or torque can be exerted onto the capsule by applying an external magnetic field. The capsule can be advanced without contact within the patient by targeted application of force and there it can accordingly achieve medical objectives.

The external magnetic field for exerting a force onto the capsule is produced by a so-called guidance magnet, which is arranged outside of the patient. A corresponding solenoid system has been disclosed in e.g. DE 103 40 925 B3.

The inventors considered a specific application of MGCE, namely esophagogastroduodenoscopy (EGD), in which it is precisely only esophagus and stomach and optionally also the duodenum of a patient that can be reached with the aid of capsule endoscopy.

For the purpose of such an EGD examination, the stomach is filled, e.g. half full or more, with water. The capsule has a volume of approximately 2-3 cm$^3$. The endoscopy capsule with a mass of approximately 2-3 g is embodied with an appropriate density which is close to, preferably just below, that of water. The endoscopy capsule then floats in the water in the stomach and, together with its buoyancy, has an effective mass of e.g. –0.1 g. The installed equipment in the capsule is arranged such that the center of gravity of the capsule on the longitudinal axis of the capsule is situated at a slight distance from the center of the capsule. The elongated capsule is therefore perpendicular in the water if no external forces are applied; the camera thereof installed at the tip faces downward in the rest state.

By using an appropriate guidance magnet, it is possible to pull the capsule below the water surface in the stomach against its buoyancy, displace it horizontally and tilt it. In this corresponding specific application of MGCE, only substantially reduced forces need to be exerted onto the capsule in comparison to the case in which the latter is to be moved through the whole intestinal tract of the patient.

Compared to the aforementioned general solenoid system, the present EGD application therefore merely makes use of a so-called EGD guidance magnet which can have a substantially simpler design than the one described in DE 103 40 925 B3. By way of example, DE 10 2008 004 871 A1 has disclosed a coil arrangement for contactless guidance of an endoscopy capsule. Furthermore, by way of example, use is made in a corresponding magnet system of a coil cooling concept from DE 10 2007 007 801 A1.

Moreover, WO 2006/014011 A1 has disclosed an alternative EGD guidance magnet: the magnet system consists of three coils, which, together, form a so-called block magnet. This block magnetic is arranged under a patient table and can, below the latter, be mechanically displaced in two dimensions. The patient table can alternatively be displaced relative to the block magnet in two dimensions. The access to a patient, who is arranged on the upper side of the patient table, is not impeded by the block magnet.

SUMMARY

One possible object is to specify a more improved solenoid system for magnetically guided capsule endoscopy.

The inventors propose a solenoid system, which serves to generate the magnetic fields for magnetically guided capsule endoscopy. The solenoid system has the components presented below, wherein all components are arranged under, i.e. on the underside of, a patient table, wherein a patient can lie on the upper side thereof. The table top of the patient table in this case defines a—generally horizontal—flat plane, but it does not need to be flat itself. By way of example, the flat plane can be defined by the outer longitudinal edges of the patient table.

The solenoid system comprises a central coil, the normal direction of which is perpendicular to the flat plane. In other words, the central coil is arranged parallel below the patient table. The solenoid system moreover has four coil pairs, likewise arranged under the table, which are arranged around the central coil in a cross-like fashion. Each coil pair comprises two single coils, the normal directions of which run parallel to the flat plane and additionally are offset by 90° with respect to one another. In other words, the coil pairs thus are formed of crossed single coils, which respectively are perpendicular to the central coil. Hence the central coil and one coil pair are, pair-wise, perpendicular to one another and therefore cover all spatial directions for magnetic fields. There are no coils above and to the side of the patient table.

Let a Cartesian coordinate system (x, y, z) be assumed for explanatory purposes: The patient table is situated in the (x, z)-plane of the coordinate system with its horizontal flat plane. The y-direction forms the vertical and thus the surface normal to the patient table. Then, the central coil is also oriented in the y-direction, i.e. the surface normal of the plane spanned by the coil points in the y-direction. The single coils of the coil pairs are accordingly respectively oriented in the x- and z-direction.

The proposals therefore relate to the idea or conceptual design of the coil geometry and arrangement. As a result of this, maximum accessibility to the patient is afforded during an examination or procedure that is to be carried out on the patient because the magnet, i.e. the whole solenoid system, is completely arranged or "hidden" under the examination table. The proposed solenoid system may have only nine coils compared to 10 or 12 coils in known systems. In contrast to the aforementioned known concept of the block magnet, the coil system is rigidly arranged, i.e. the guidance magnet does not contain any mechanically moveable parts.

However, compared to a system that surrounds the patient, it is necessary, for the coils, to use amplifiers with a greater maximum current and power, having approximately 350 A and 40 kW compared to 90 A and 10 kW.

Each single coil of a coil pair has a section that is closest to the flat plane, i.e. it is situated nearest to the flat plane. In a preferred embodiment, this section runs parallel to the flat plane. Hence the single coil has at least one flat section, which is arranged as closely as possible to the patient table and can therefore produce a field that is as strong as possible in the region of the patient. The remaining coil parts run away from the flat plane or the patient table, and the field components thereof are pushed into the background on the upper side of the patient table.

In a further preferred embodiment, the central coil and/or the single coils have a rectangular shape with rounded corners. Thus, the winding of the coils runs along a curve which approximately describes a rectangle, or the area delimited by the winding is approximately rectangular. These then have a side, i.e. a section, that is arranged closest to the flat plane or the examination table and runs parallel to the latter, particularly for the single coils. Adjacent to this section there are then the two sides of the rectangle running perpendicular thereto; however, these produce field components that are offset by 90° as a result of the 90° angle in the rectangle. The fourth side of the rectangle is then situated as far away as possible from the flat plane in order, in practical terms, to attenuate the field generated by the first section only weakly.

In the embodiment of the central coil as a rectangle or square, it is possible, in particular, for the four coil pairs to be arranged at the corners of the central coil in a cross-like fashion. The single coils are then aligned parallel to the respective sides of the rectangular central coil.

In a further preferred embodiment, the respectively one single coil of a coil pair is inserted into the respectively other single coil. This makes the production of the coil pair particularly simple because there is no need to cross the windings.

In a further advantageous embodiment, all coil pairs have the same alignment. By way of example, using the aforementioned nomenclature of a central coil oriented in the y-direction, all first coils of the four coil pairs are aligned in the x-direction and all second coils of the four coil pairs are aligned in the z-direction. This produces a very symmetric arrangement.

In a further preferred embodiment, the central coil and/or the single coil is a racetrack coil. Racetrack coils are planar and can, for example, be embodied as aluminum or copper strip winding.

Thus, in a preferred variant, the racetrack coil has a strip winding.

In a preferred embodiment, the strip winding is cooled on one or on both lateral sides of the strip winding. In the case of one-sided cooling, the cooling is brought about on that side of the strip winding which results in a design of the coil arrangement that is as compact as possible with the smallest possible distance from the work volume.

BRIEF DESCRIPTION OF THE DRAWINGS

These and other objects and advantages of the present invention will become more apparent and more readily appreciated from the following description of the preferred embodiments, taken in conjunction with the accompanying drawings of which:

FIG. 2 shows the solenoid system from FIG. 1 in the direction of the arrow II.

DETAILED DESCRIPTION OF THE PREFERRED EMBODIMENT

Figure 1:
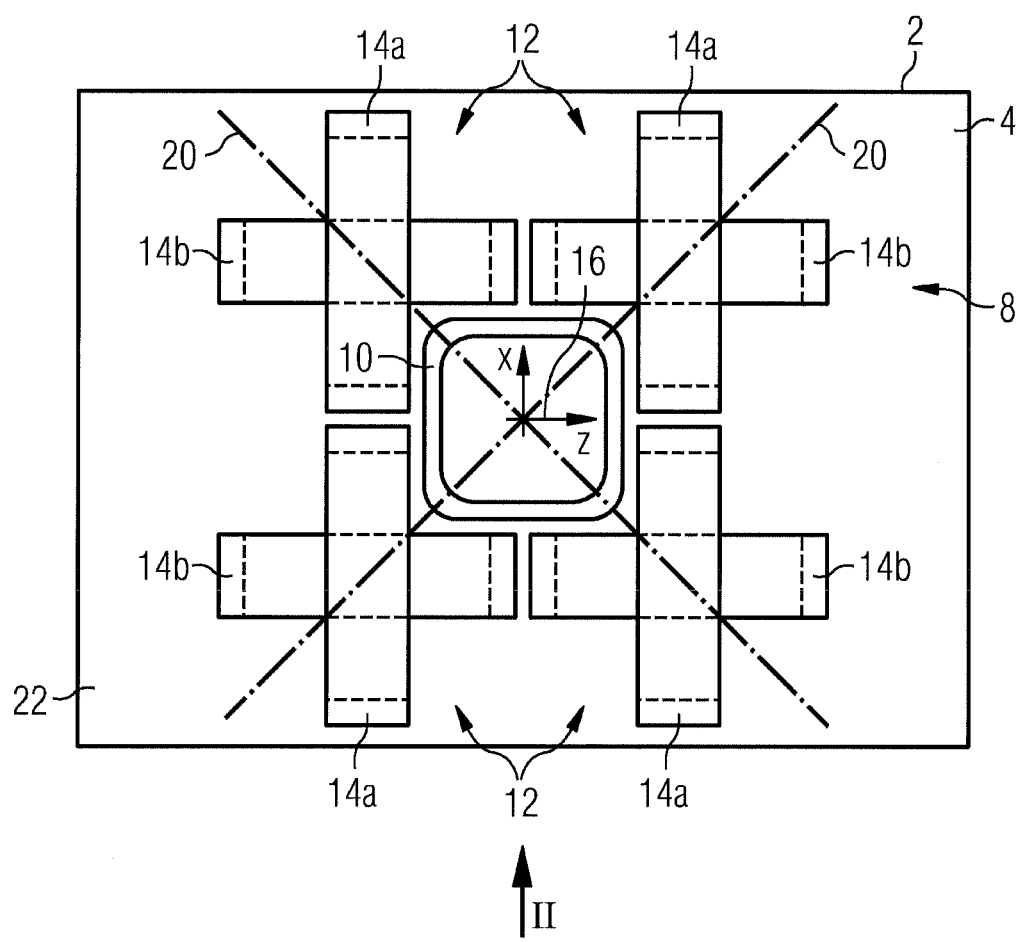
FIG. 1 shows a plan view of a patient table with a solenoid system according to the inventors' proposals.

Reference will now be made in detail to the preferred embodiments of the present invention, examples of which are illustrated in the accompanying drawings, wherein like reference numerals refer to like elements throughout.

FIGS. 1 and 2 respectively show a patient table 2, in the direction of viewing arrows I and II, on the upper side 4 of which magnetically guided capsule endoscopy (MGCE) is to be performed on a patient (not illustrated). In order to exert a force on the capsule (not illustrated), a solenoid system 8 has been attached to the lower side 6 of the patient table 2 in a stationary fashion. The patient table, or the table top thereof, spans a flat plane 22.

The solenoid system 8 comprises a central coil 10 and four coil pairs 12, which respectively include a first single coil 14a and a second single coil 14b. Here, the single coils 14b have respectively been inserted into the single coils 14a. In respect of the orientation of a coordinate system 16, the central coil 10 is an Hy-coil, i.e. the normal direction thereof points in the y-direction. The single coils 14a are Hz-coils; the single coils 14b are Hx-coils.

In an alternative embodiment (not illustrated), the coils 14a are inserted into the coils 14b. In the exemplary embodiment all single coils 14a, b and the central coil 10 respectively have a rectangular shape, which, in particular, can be seen for the central coil 10 in FIG. 1 and for the two illustrated single coils 14b in FIG. 2. In FIG. 2, the rectangular shape is symbolized by the line of the rectangle 18 for the single coil 14b.

All coils are embodied as so-called racetrack coils, i.e. they are planar and embodied with an aluminum or copper strip winding. The coil dimensions specified below relate to a copper winding—which need not necessarily be a strip winding—with an assumed space factor, including cooling, of 85%. The external dimensions of the central coil 10 in x- and z-direction are respectively approximately 60 cm. The coil packet has a width of approximately 10 cm in the y-direction by 7.5 cm in the x- or z-direction. Although specific sizes are described herein, the invention is not limited to any particular dimensions.

The single coils 14a, b have a winding cross section of approximately 25 cm by 9 cm; here, the external dimensions of the single coils 14a are approximately 80 to 100 cm in the y-direction and approximately 80 cm in the x-direction. The external dimensions of the single coils 14b are approximately 60 to 80 cm in the y-direction and approximately 80 cm in the z-direction.

It is possible to identify in FIG. 1 how the coil pairs 12 are grouped around the central coil 10 in respect of the flat plane 22 in a cross-like fashion, indicated by the cross 20. Here, the cross 20 meets the respective corners of the central coil 10. In the region of the patient table 2, the respectively closest, i.e. top-most, sections of the single coils 14a, b respectively run parallel to one side of the central coil 10.

FIGS. 1 and 2 also make it possible to identify both that the central coil 10 lies parallel to the flat plane 22 and also that the respective top sections 24 of the single coils 14a, b, which lie closest to the patient table, respectively run parallel to the flat plane 22.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV*, 69 USPQ2d 1865 (Fed. Cir. 2004).

The invention claimed is:

1. A solenoid system for a magnetically guided capsule endoscopy, comprising the following components arranged under a patient table defining a flat plane:
a central coil with a normal direction perpendicular to the flat plane; and
four coil pairs, which are arranged around the central coil with respect to the flat plane, each coil pair comprising first and second single coils, each of the first and second coils having a normal direction oriented parallel to the flat plane, the normal direction of the first coil being offset by 90° with respect to the normal direction of the second coil, wherein the central coil has a rectangular shape defining four corners, the four coil pairs are formed respectively at the four corners of the central coil in a cross configuration, the cross configuration is formed by first and second imaginary lines, which each bisects the central coil, the first imaginary line extends from a first coil pair to a third coil pair, through first and third opposite corners of the central coil, and the second imaginary line extends from a second coil pair to a fourth coil pair, through second the fourth opposite corners of the central coil.

2. The solenoid system as claimed in claim 1, wherein each single coil has a section closest to the flat plane, which runs parallel to the flat plane.

3. The solenoid system as claimed in claim 1, wherein the central coil and/or each single coil has a rectangular cross-sectional shape.

4. The solenoid system as claimed in claim 1, wherein within each coil pair, the first single coil has a larger cross sectional dimension than the second single coil, and within each coil pair, the second single coil extends through the first single coil.

5. The solenoid system as claimed in claim 4, wherein within each coil pair, the first single coil has a larger height cross sectional dimension than the second single coil.

6. The solenoid system as claimed in claim 1, wherein all coil pairs have the same alignment such that the first coils have normal directions that are parallel to one another and the second coils have normal directions that are parallel to one another.

7. The solenoid system as claimed in claim 1, wherein the central coil and/or each single coil is a racetrack coil.

8. The solenoid system as claimed in claim 7, wherein the racetrack coil has a strip winding.

9. The solenoid system as claimed in claim 8, wherein the strip winding is cooled on one or on both lateral sides of the strip winding.

10. The solenoid system as claimed in claim 2, wherein the central coil and/or each single coil has a rectangular cross-sectional shape.

11. The solenoid system as claimed in claim 10, wherein within each coil pair, the first single coil has a larger height than the second single coil, and within each coil pair, the second single coil extends through the first single coil.

12. The solenoid system as claimed in claim 11, wherein all coil pairs have the same alignment such that the first coils have normal directions that are parallel to one another and the second coils have normal directions that are parallel to one another.

13. The solenoid system as claimed in claim 12, wherein the central coil and/or each single coil is a racetrack coil.

14. The solenoid system as claimed in claim 13, wherein the racetrack coil has a strip winding.

15. The solenoid system as claimed in claim 14, wherein the strip winding is cooled on one or on both lateral sides of the strip winding.

16. The solenoid system as claimed in claim 1, wherein the central coil and the four coil pairs are stationary with respect to the patient table.

17. The solenoid system as claimed in claim 1, wherein for each of the four coil pairs, a pocket is formed where the first coil intersects the second coil, and for each of the four coil pairs, one of the four corners of the central coil is situated in the pocket.

18. The solenoid system as claimed in claim 17, wherein for each of the four coil pairs, the first coil has two sides extending from where the first and second coils intersect, for each of the four coil pairs, the second coil has two sides extending from the where the first and second coils intersect, for each of the four coil pairs, one side of the first coil partially overlaps and runs parallel with a first corner side of the central coil, and for each of the four coil pairs, one side of the second coil partially overlaps and runs parallel to a second corner side of the central coil, the second corner side being adjacent to and perpendicular with the first corner side.

19. The solenoid system as claimed in claim 1, wherein the central coil has four sides, for each of the four coil pairs, the first coil extends parallel to first and third sides of the central coil, and for each of the four coil pairs, the second coil extends parallel to second and fourth sides of the central coil.

20. The solenoid system as claimed in claim 1, wherein the solenoid system magnetically guides a capsule in first, second and third mutually perpendicular directions, the central coil magnetically guides the capsule in the first direction, the first coils of the four coil pairs magnetically guide the capsule in the second direction, and the second coils of the four coil pairs magnetically guide the capsule in the third direction.

\* \* \* \* \*